US009763958B2

(12) United States Patent
Likitlersuang et al.

(10) Patent No.: US 9,763,958 B2
(45) Date of Patent: *Sep. 19, 2017

(54) PRESERVATIVE FREE BIMATOPROST AND TIMOLOL SOLUTIONS

(71) Applicant: Allergan, Inc., Irvine, CA (US)

(72) Inventors: Sukhon Likitlersuang, Irvine, CA (US); Ajay Parashar, Irvine, CA (US); Chetan P. Pujara, Irvine, CA (US); William F. Kelly, Rancho Santa Margarita, CA (US); Jie Shen, Irvine, CA (US); Marina Bejanian, Laguna Niguel, CA (US); Rhett Schiffman, Laguna Beach, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,919

(22) Filed: Apr. 21, 2015

(65) Prior Publication Data

US 2015/0224115 A1    Aug. 13, 2015

Related U.S. Application Data

(63) Continuation of application No. 13/785,911, filed on Mar. 5, 2013, now Pat. No. 9,061,034, which is a continuation-in-part of application No. 13/812,597, filed as application No. PCT/US2011/045654 on Jul. 28, 2011, now Pat. No. 9,078,854.

(60) Provisional application No. 61/368,685, filed on Jul. 29, 2010.

(51) Int. Cl.
| | |
|---|---|
| A61K 31/5575 | (2006.01) |
| A61K 31/5377 | (2006.01) |
| A61K 9/00 | (2006.01) |
| A61K 47/12 | (2006.01) |
| A61K 47/02 | (2006.01) |
| A61K 9/08 | (2006.01) |

(52) U.S. Cl.
CPC ........ *A61K 31/5575* (2013.01); *A61K 9/0048* (2013.01); *A61K 9/08* (2013.01); *A61K 31/5377* (2013.01); *A61K 47/02* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 4,494,274 A | 1/1985 | Thurlow | |
| 4,599,353 A | 7/1986 | Bito | |
| 4,952,581 A | 8/1990 | Bito et al. | |
| 4,994,274 A | 2/1991 | Chan et al. | |
| 5,028,624 A | 7/1991 | Chan et al. | |
| 5,034,413 A | 7/1991 | Chan et al. | |
| 5,268,624 A | 12/1993 | Zanger et al. | |
| 5,352,708 A | 10/1994 | Woodward et al. | |
| 5,688,819 A * | 11/1997 | Woodward | 514/357 |
| 6,051,576 A | 4/2000 | Ashton et al. | |
| 6,184,250 B1 | 2/2001 | Klimko et al. | |
| 6,248,735 B1 | 6/2001 | Baldwin et al. | |
| 8,309,605 B2 | 11/2012 | Chang et al. | |
| 8,309,635 B2 * | 11/2012 | Gelbin | C08K 5/526 252/182.14 |
| 8,618,093 B2 | 12/2013 | Chen et al. | |
| 8,629,140 B2 | 1/2014 | Chen et al. | |
| 8,906,907 B2 | 12/2014 | Chen et al. | |
| 9,061,034 B2 * | 6/2015 | Likitlersuang | A61K 47/12 |
| 9,078,854 B2 * | 7/2015 | Likitlersuang | A61K 9/0048 |
| 2004/0082660 A1 | 4/2004 | Ueno | |
| 2010/0210720 A1 | 8/2010 | Pilotaz et al. | |
| 2015/0224115 A1 | 8/2015 | Likitlersuang et al. | |
| 2016/0113934 A1 | 4/2016 | Likitlersuang et al. | |

FOREIGN PATENT DOCUMENTS

| | | | | |
|---|---|---|---|---|
| CA | 2426049 | 5/2002 | | |
| EP | 0286903 | 10/1988 | | |
| EP | 0364417 | 4/1990 | | |
| EP | 0458590 | 11/1991 | | |
| EP | 0509752 | 10/1992 | | |
| EP | 0590972 | 4/1994 | | |
| EP | 1057486 | 6/2000 | | |
| EP | 0660716 | 11/2001 | | |
| EP | 2127638 | 12/2009 | | |
| EP | 2567689 | 3/2013 | | |
| FR | 2918891 | 1/2009 | | |
| FR | 2918891 A1 * | 1/2009 | ........... | A61K 9/0048 |
| JP | 08-501310 | 3/1994 | | |
| JP | EP 2127638 A1 * | 12/2009 | ........... | A61K 9/0048 |
| WO | 9406433 | 3/1994 | | |
| WO | 9520378 | 8/1995 | | |
| WO | 97-30710 | 8/1997 | | |
| WO | 98-25620 | 6/1998 | | |
| WO | 00-04898 | 2/2000 | | |
| WO | 00-54810 | 9/2000 | | |

(Continued)

OTHER PUBLICATIONS

Ganfort® 0.3-5 Eye Drops, May 2009.*
LumiganTM Package Insert, NDA 21-275, Mar. 2001.*
Kuppens et al., Effect of timolol with and without preservative on the basal tear turnover in glaucoma, Br J Ophthalmol 1995;79:339.*
U.S. Appl. No. 14/733,188, filed Apr. 2015, Likitlersuang et al.*
Alexander, Christy et al, Prostaglandin Analog Treatment of Glaucoma and ocular Hypertension, Ann Pharmacother, 2002, 504-511, 35.
Ashton, Paul et al, Formulation Influence on Conjunctival Penetration of Four Beta Blockers in the Pigmented Rabbit: A Comparison with Corneal Penetration, Pharmaceutical Research, 1991, 1166-1174, 8 (9).

(Continued)

*Primary Examiner* — Svetlana M Ivanova
(74) *Attorney, Agent, or Firm* — Lorenz Siddiqi

(57) ABSTRACT

The present invention is directed to preservative-free solutions of bimatoprost and timolol for lowering intra-ocular pressure and treatment of glaucoma.

5 Claims, No Drawings

(56) References Cited

FOREIGN PATENT DOCUMENTS

| WO | 02-092098 | 11/2002 |
| WO | 2007-042262 | 4/2007 |
| WO | 2012-015998 | 2/2012 |

OTHER PUBLICATIONS

Bean, Gerald, Commercially Available Prostaglandin Analogs for the Reduction of Intraocular Pressure: Similarities and Differences, Survey of Ophthalmology, 2008, S69-S84, 53 (Supp. 1).

Bito, LZ, Esterified Prostaglandin Shows 'Potent' Promise, Pharmacology Prodrugs, 1989, 2 Pages, 5.

Bito, LZ, Biological Protection with Prostanoids, CRC Press, Inc., 1985, 231-252, 1, Cohen, M. M., ed., Boca Raton, Fla.

Bito, LZ, Prostaglandins, Old Concepts and New Perspectives, Archives of Ophthalmology, 1987, 1036-1039, 105.

Bito, LZ, Prostaglandins, Other Eicosanoids, and Their derivatives as Potential Antiglaucoma Agents, Glaucoma: Applied Pharmacology, 1984, 477-505, 20.

Calissendorff, Berit et al, Bioavailability in the Human Eye of a Fixed Combination of Latanoprost and Timolol Compared to Monotherapy, Journal of Ocular Pharmacology and Therapeutics, 2002, 127-131, 18(2).

Campbell, S.H. et al, Double-Masked Three-Period Crossover Investigation of Timolol in Control of Raised Intraocular Pressure, Eye, 1993, 105-108, 7.

Cantor, Louis et al, Bimatoprost: A Member of a New Class of Agents, The Prostamides, for Glaucoma Management, Exp. Opin. Invest. Drugs, 2001, 721-731, 10 (4).

Chiou, G.C., Development of D-Timolol for the Treatment of Glaucoma and Ocular Hypertension, J. Ocul. Pharmacol., 1990, 67-74, 6 (1).

Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).

Eisenberg, Dan, Bimatoprost and Travoprost: A Review of Recent Studies of Two New Glaucoma Drugs, Survey of Ophthalmology, 2002, S105-S115, 47 (1).

Heijl, Anders et al, Reduction of Intraocular Pressure and Glaucoma Progression: Results From the Early Manifest Glaucoma Trial, Arch Ophthalmol, 2002, 1268-1279, 120.

Hommer, A., Bimatoprost: Erste Wirksubstanz Einer Neuen Stoffklasse, Der Prostamide Fur Die Glaukombehandlung, Spektrum Augenheilkd, 2001, 146-149, 15.

Kass, Michael et al, The Ocular Hypertension Treatment Study: A Randomized Trial Determines That Topical Ocular Hypotensive Medication Delays or Prevents the Onset of Primary Open-Angle Glaucoma, Arch. Ophthalmol., 2002, 701-713, 120.

Komoto, Junichi, Prostaglandin F2α Formation From Prostaglandin H2 by Prostaglandin F Synthase (PGFS): Crystal Stucture of PGFS Containing Bimatoprost, American Chemical Society, Feb. 21, 2006, 1987-1996, 45 (7).

Krauss, Achim, Update on the Mechanism of Action of Bimatoprost: A Review and Discussion of New Evidence, Surv. Ophthalmol., 2004, S5-S11, 49 (Supp. 1).

Laibovitz, Robert, Comparison of the Ocular Hypotensive Lipid AGN 192024 With Timolol, Arch Ophthal, 2001, 994, 119.

Larsson, Lil-Inger, The Effect on Diurnal Intraocular Pressure of the Fixed Combination of Latanoprost 0.005% and Timolol 0.5% in Patients With Ocular Hypertension, Acta Ophthalmol. Scand., 2001, 125-128, 79.

Leske, Cristina et al, Predictors of Long-Term Progression in the Early Manifest Glaucoma Trial, Ophthalmology, 2007, 1965-1972, 114.

Leske, M. Cristina et al, Factors for Glaucoma Progression and the Effect of Treatment: The Early Manifest Glaucoma Trial, Ophthalmology, 2003, 1965-1972, v114, #11.

Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).

Mills, K.B., Blind Randomised Non-Crossover Long-Term Trial Comparing Topical Timolol 0.25% with Timolol 0.5% in the Treatment of Simple Chronic Glaucoma, British Journal of Ophthalmology, Apr. 1983, 216-219, 67(4).

Nilsson, Siv, PGF 2α Increases Uveoscleral Outflow, Invest. Ophthalmol. Vis. Sci, 1987, 284, 28 (Suppl).

Ota, Takashi, The Effects of Prostaglandin Analogues on IOP in Prostanoid FP-Receptor-Deficient Mice, Invest. Ophthalmol. Vis. Sci., 2005, 4159-4163, 46.

Resul, et al., Structure-Activity Relationships of Prostagladin Analogues as Ocular Hypotensive Agents, Current Opinion in Therapeutic Patents, 1993, 781-795, US.

Sharif, Najam, Bimatoprost (Lumigan®) is an Agonist at the Cloned Human Ocular FP Prostaglandin Receptor : Real-Time FLIPR-Based Intracellular Ca2+ Mobilization Studies, Prostaglandins, Leukotrienes and Essential Fatty Acids, 2003, 27-33, 68.

Sharif, Najam, Bimatoprost and Its Free Acid Are Prostaglandin FP Receptor Agonists, European Journal of Pharmacology, 2001, 211-213, 432.

Sorbera, L.A., Bimatoprost, Drugs of the Future, 2001, 433-439, 26 (5).

Starr, Michael, Further Studies on the Effects of Prostagladin on Intraocular Pressure in the Rabbit, Exp. Eye Res., 1971, 170-177, 11.

The AGIS Investigators, The Advanced Glaucoma Intervention Study (AGIS): 7. The Relationship Between Control of Intraocular Pressure and Visual Field Deterioration, Am. J. Ophthalmol., 2000, 429-440, 130.

Woodward, David, Pharmacological Characterization of a Novel Antiglaucoma Agent, Bimatoprost (AGN 192024), J. Pharmacol. Exp. Ther., Jan. 24, 2003, 772-785, 305 (2).

Alm, A. et al, Effects of D-Timolol and L-Timolol Eye Drops on Intraocular Pressure and Aqueous Flow. A Dose-Response Study in Normal Eyes. Acta Ophthalmol (Copenh)., Feb. 1990, 19-22, 68(1).

Stewart, W.C., Timolol Hemihydrate: a New Formulation of Timolol for the Treatment of Glaucoma., J Ocul Pharmacol Ther., Summer 1996, 225-237, 12(2).

Lumigan Package Insert, Mar. 2001, 6 Pages, NDA 21-275.

Zimmerman, T.J. et al, Timolol Maleate: Efficacy and Safety, Arch Ophthalmol, Apr. 1979, 656-658, 97(4).

European Medicines Agency, European Public Assessment Report Ganfort, Retrieved on Oct. 22, 2014 From http://www.emea.europa.eu/humandocs/PDFs/EPAR/ganfort/066806en1.pdf. 3 Pages.

Jaenen, N. et al, Ocular Symptoms and Signs with Preserved and Preservative-Free Glaucoma Medications, European Journal of Ophthalmology, 2007, 341-349, 17(3).

Leung, Eamon et al, Prevalence of Ocular Surface Disease in Glaucoma Patients, J Glaucoma, 2008, 350-355, 17.

Liang, Hong et al, Comparison of the Ocular Tolerability of a Latanoprost Cationic Emulsion Versus Conventional Formulations of Prostaglandins: An in Vivo Toxicity Assay, Molecular Vision, 2009, 1690-1699, 15.

Brasnu, Emmanuelle, In Vitro Effects of Preservative-Free Tafluprost and Preserved Latanoprost, Travoprost, and Bimatoprost in a Conjunctival Epithelial Cell Line, Current Eye Research, Apr. 1, 2008, 303-312, 33 (4).

International Search Report and Written Opinion mailed on Apr. 23, 2014 for PCT/US14/20210 filed Mar. 4, 2014 in the name of Allergan, Inc.

International Search Report and Written Opinion mailed on Feb. 16, 2012 for PCT/US11/45654 filed Jul. 28, 2011 in the name of Allergan, inc.

Kuppens, E.V. et al, Effect of Timolol With and Without Preservative on the Basal Tear Turnover in Glaucoma, Br. J. Ophthalmol, 1995, 339-342, 79.

Letchinger, Susan et al, Can the Concentration of Timolol or the Frequency of Its Administration Be Reduced?, Ophthalmology, 1993, 1259-1262, 100.

Remington, The Science and Practice of Pharmacy, 20th ed. at 829 (2000).

(56) References Cited

OTHER PUBLICATIONS

Abelson, M.B., The Secret World of Pharmacokinetics: Knowing something about this area of research can help make a better clinician, Rev. Opthalmol. 2009, 10 pages.
Katsanos, Andreas, Bimatoprost and Bimatoprost/Timolol Fixed Combination in Patients with Open-angle Glaucoma and Ocular Hypertension, J. Ocular Pharmacology & Therapeutics, 2011, 67-71, 27.
EP1392319 B1, Rejection of the Opposition (Art. 101(2) EPC), Dec. 17, 2013, 13 Pages.
Ganfort®—Package Leaflet 2008, 2 pages.
Brandt, James D., Bimatoprost/Timolol Fixed Combination: A 3-month Double-masked, Randomized Parallel Comparison to Its Individual Components in Patients With Glaucoma or Ocular Hypertension, J. Glaucoma, 2008, 211-216, 17 (3).
Chen, June, Bimatoprost: Mechanism of Ocular Surface Hyperemia Associated with Topical Therapy, Cardiovascular Drug Reviews, 2005, 231-246, 23 (3).
Lewis, Richard A., The Safety and Efficacy of Bimatoprost/Timolol Fixed Combination: A1-yearf Double-masked, Randomized Parallel Comparison to Its Individual Components in Patients with Glaucoma or Ocular Hypertension, J. Glaucoma, 2010, 424-426, 19.
Rulo, Alexandar, et al., Additive effect of latanoprost, a prostaglandin F2α, analogue, and timolol in patients with elevated intraocular pressure, Br. J. Ophthalmol., 1994, 899-902, 78.
Woodward, David et al, The Pharmacology of Bimatoprost (LumiganTM), Surv Ophthalmol, 2001, S337-S345, Suppl 4.

\* cited by examiner

PRESERVATIVE FREE BIMATOPROST AND TIMOLOL SOLUTIONS

CROSS REFERENCE TO RELATED APPLICATIONS

This Application is a continuation of U.S. patent application Ser. No. 13/785,911, filed Mar. 5, 2013, which is a continuation-in-part of U.S. patent application Ser. No. 13/812,597, filed Jan. 28, 2013, which is a national phase application under 35 U.S.C. §371 of PCT Patent Application Serial No. PCT/US11/45654, filed Jul. 28, 2011, which claims priority to Provisional Patent Application Ser. No. 61/368,685, filed Jul. 29, 2010, all of which are hereby incorporated by reference in their entirety.

FIELD OF THE INVENTION

The present application is directed to preservative-free formulations of bimatoprost and timolol.

BACKGROUND OF THE INVENTION

Bimatoprost is a prostamide, a synthetic analog of prostaglandin $F_{2\alpha}$ ($PGF_{2\alpha}$), with potent ocular hypotensive activity. Bimatoprost lowers intraocular pressure (TOP) in patients with glaucoma or ocular hypertension by increasing outflow of aqueous humor through both the trabecular meshwork and uveoscleral routes. Timolol is a non-selective beta-adrenergic receptor blocker and functions by reducing aqueous humor production through blockage of the beta receptors on ciliary epithelium.

Use of preservative containing eye drops has been implicated in the development or worsening of ocular surface disease. Management of open angle glaucoma and ocular hypertension require long term treatment with eye drops containing preservatives. Symptoms and signs of ocular surface disease such as ocular surface breakdown, irritation, burning, foreign body sensation, dryness, inadequate quantity of tears, etc. are prevalent in a large proportion of patients with open angle glaucoma and ocular hypertension.

Compared to eye drops preserved with benzalkonium chloride, preservative-free eye drops induce significantly fewer ocular symptoms and signs of irritation in patients, such as pain or discomfort, foreign body sensation, stinging or burning, and dry eye sensation.

Patients experiencing hypersensitivity reactions with benzalkonium chloride cannot use a commercial bimatoprost product containing benzalkonium chloride which is preserved even with 0.005% w/v benzalkonium chloride. Benzalkonium chloride also may be absorbed by the soft contact lenses therefore patients wearing soft contact lenses are advised to remove lenses prior to administration and wait at least 15 minutes before reinserting them.

SUMMARY OF THE INVENTION

The present invention is directed to a bimatoprost and timolol solutions without benzalkonium chloride or any other preservative which will be superior from a safety and tolerability standpoint while at least maintaining and/or improving its efficacy of IOP lowering and be available for use by patients hypersensitive to benzalkonium chloride and be convenient for patients wearing soft contact lenses.

Bimatoprost and timolol ophthalmic solution without preservative is a clear to slightly yellow, isotonic, sterile solution. The drug product contains bimatoprost and timolol as the active ingredients. The inactive ingredients are tonicity and buffer agents, and purified water. Suitable buffers such as sodium phosphate dibasic heptahydrate and citric acid monohydrate and suitable tonicity agents such as sodium chloride may be included. The solution is an aqueous solution having a pH value within the range of about 7 to about 8, and preferably about 7.3. Suitable buffers may be included, such as sodium phosphate dibasic heptahydrate, citric acid monohydrate. Preferably, the tonicity agent such as sodium chloride will be employed in an amount to provide a final osmotic value of at least about 200 mOsm/kg, preferably from about 280 to about 370 mOsm/kg.

The present invention can be made generally according to the teachings of U.S. patent application Ser. No. 10/153,043 which is hereby incorporated by reference in its entirety.

Some embodiments of the invention include the following:

1) A preservative free bimatoprost and timolol composition for lowering intraocular pressure in a human patient comprising the following formulation: about 0.03% w/v bimatoprost; about 0.5% timolol and having no preservative.
2) The preservative free bimatoprost and timolol solution of paragraph 1 for lowering intraocular pressure in a human patient comprising the following formulation: 0.03% w/v bimatoprost; 0.5% timolol; 0.268% w/v Sodium Phosphate Dibasic Heptahydrate; 0.014% Citric Acid Monohydrate; about 0.68% sodium chloride, hydrochloric acid, water, sodium hydroxide and having a pH of about 7.3.
3) The preservative free bimatoprost and timolol solution of paragraphs 1 and 2, wherein the timolol is timolol maleate at 0.68% w/v.
4) A composition as described in Table 1.
5) The bimatoprost and timolol solution of paragraphs 1-4, wherein the solution is useful for treating glaucoma.
6) The bimatoprost and timolol composition of paragraphs 1-4, wherein the composition is a solution wherein the solution is contained in a unit dose kit form.
7) The bimatoprost and timolol composition of any of paragraphs 1-6, wherein the composition is applied once a day to each eye.
8) The bimatoprost and timolol composition of any of paragraphs 1-6, wherein the composition is applied twice a day to each eye.
9) The bimatoprost and timolol compositions of paragraphs 1-4, wherein the composition has greater bioavailability of bimatoprost and timolol in the eye of the patient with fewer side-effects than bimatoprost and timolol preserved with benzalkonium chloride or another preservative.
10) The composition of paragraph 1, wherein the composition may be a solution, emulsion, dispersion, suspension, reverse emulsion and microemulsion.
11) The composition of paragraph 1, wherein the composition is contained in a unit-dose vial.
12) The composition of paragraph 1, wherein the composition is contained in a multi-dose vial which has anti-preservative properties such as metal-ions imbedded in its dispensing tip.
13) The composition of paragraph 12, wherein the metal ions are silver ions.
14) The bimatoprost and timolol composition of paragraph 1, wherein the composition has better intraocular lowering ability and fewer side-effects than the same composition preserved with benzalkonium chloride.

DETAILED DESCRIPTION OF THE INVENTION

A bimatoprost and timolol ophthalmic formulation of the present invention without preservative is shown in Table 1.

TABLE 1

Example of bimatoprost and timolol ophthalmic solution without preservative according to the present invention:

| Ingredients | Units | Grade | Amount |
|---|---|---|---|
| Bimatoprost | % w/v | N/A | 0.03 |
| Timolol Maleate | % w/v | USP/Ph Eur | 0.68 |
| Sodium Phosphate Dibasic Heptahydrate | % w/v | USP | 0.268 |
| Citric Acid Monohydrate | % w/v | USP/Ph Eur | 0.014 |
| Sodium Chloride | % w/v | USP/Ph Eur | 0.68 |
| Hydrochloric Acid | % w/v | USP/P Eur | pH 7.3 |
| Sodium Hydroxide | % w/v | USP/Ph Eur | pH 7.3 |
| Purified Water/WFI | Q.S. | USP/Ph Eur | QS |

The present invention is directed to formulations of bimatoprost and timolol without benzalkonium chloride as a preservative and may be marketed in unit dose form. As a result of the removal of benzalkonium chloride, the present invention results in the same as or greater bioavailability of the active ingredients bimatoprost and timolol in the eye without the unwanted side-effects associated with the preservative benzalkonium chloride such as hyperemia, which will improve efficacy of the product in lowering IOP per dosage unit, with superior patient compliance and fewer side-effects. Other side effects which may be avoided with the preservative free compositions of the present invention include, blepharitis, corneal erosion, depression, epiphora, eye discharge, eye dryness, eye irritation, eye pain, hypermia, allergic conjunctivitis, eyelid edema, eyelid erythema, eyelid pruritus, foreign body sensation, headache, hypertension, oral dryness, somnolence, superficial punctate keratitis, and visual disturbance.

EXAMPLE 1

Ganfort® is a fixed combination of bimatoprost 0.03% timolol 0.5% with 50 ppm benzalkonium chloride (BAK, as preservative) used in a number of countries worldwide as an effective treatment for the reduction of intraocular pressure (TOP) in patients with open-angle glaucoma or ocular hypertension (OHT). A preservative-free (PF) formulation of Ganfort®, hereafter referred to as Ganfort® PF, has been developed to cater to diverse patients needs. Ganfort® PF is the same formulation as that of Ganfort®, except for the removal of 50 ppm BAK. The use of a preservative-free formulation is preferred for patients who have a known sensitivity to preservatives or where preservative use is a concern particularly in patients with dry eyes or other ocular surface disorders.

The IOP lowering efficacy of a PF formulation of the bimatoprost component of Ganfort® was studied: In a 5-day, 30 patient, randomized, masked, paired-eye comparison study of bimatoprost 0.03 PF with bimatoprost 0.03% (preserved with 50 ppm BAK), the treatment difference (i.e. bimatoprost PF minus bimatoprost preserved) in IOP lowering efficacy on Day 5 ranged from +0.07 mmHg to +0.53 mmHg, favoring the preserved formulation (Clinical Study Report on file); In a 12 week, 597 patient, multi-center, randomized, masked, parallel group study, the a-priori defined primary efficacy analysis of IOP change from baseline in worse eye IOP at week 12 (per protocol population), showed a treatment difference of +0.02 to +0.32 mmHg favoring bimatoprost preserved (Clinical Study Report on file). Based on the results of these studies, and the known penetration enhancing effects of BAK, it was anticipated that the removal of BAK from Ganfort® PF would result in a reduction in its IOP lowering effect, though this may not be statistically significant.

For development of Ganfort® PF, a 12 week, multi-center, randomized, masked study was conducted in 561 patients with glaucoma or ocular hypertension, comparing the efficacy and safety of Ganfort® PF with Ganfort®. IOP was measured at 3 time points (hour 0, hour 2 and hour 8), at each of the study visits (baseline, weeks 2, 6 and 12). The study was designed to test for statistical non-inferiority as well as statistical equivalence of PF formulation with preserved formulation, based on pre-established criteria using IOP margins of 1.5 mmHg, Differences in the IOP lowering effects of the two formulations (Ganfort® PF minus Ganfort®) were evaluated, where a negative difference is indicative of greater IOP lowering by Ganfort® PF.

At baseline, no statistically or clinically significant differences in worse eye IOP (identified as the eye with higher baseline IOP) or average eye IOP (average IOP of both eyes) were observed between the Ganfort® PF and Ganfort® groups. While Ganfort® PF met the criteria for statistical non-inferiority and equivalence with Ganfort® based on the a priori established statistical criteria, the differences in treatments (Ganfort® PF-Ganfort®) in IOP lowering from baseline at all of the 9 follow-up time points (hours 0, 2 and 8, at weeks 2, 6 and 12), favored Ganfort® PF:

1) In a-priori defined primary analysis at week 12 (per protocol population), the treatment difference in change from baseline in worse eye IOP was −0.30 to −0.37 mmHg;

2) Across the 12 week study (ITT population), the treatment difference in change from baseline for worse eye IOP ranged from −0.12 to −0.54 mmHg, favoring Ganfort® PF at all follow up time points; and, 3) The treatment difference in change from baseline for average eye IOP ranged from −0.19 to −0.49 mmHg during weeks 2 to 12, favoring Ganfort® PF at all follow up time points.

TABLE I

Baseline and Change From Baseline in IOP (mm Hg) in Study of Example I

| Visit | Hour | Statistic | Worse Eye IOP[a] (PP) | | | Worse Eye IOP[a] (ITT) | | |
|---|---|---|---|---|---|---|---|---|
| | | | GANFORT® PF (N = 256) | GANFORT® (N = 260) | Difference (95% CI)[c] | GANFORT® PF (N = 278) | GANFORT® (N = 283) | Difference (95% CI)[d] |
| Baseline | 0 | Mean | 25.41 | 25.38 | 0.01 | 25.34 | 25.30 | 0.08 |
| | | SD | 2.232 | 2.209 | (−0.35, 0.37) | 2.233 | 2.244 | (−0.27, 0.42) |
| | 2 | Mean | 24.79 | 24.72 | 0.04 | 24.71 | 24.61 | 0.14 |
| | | SD | 2.676 | 2.470 | (−0.38, 0.47) | 2.700 | 2.536 | (−0.27, 0.54) |
| | 8 | Mean | 23.88 | 23.82 | 0.06 | 23.81 | 23.80 | 0.06 |
| | | SD | 3.008 | 2.747 | (−0.39, 0.50) | 2.989 | 2.795 | (−0.36, 0.49) |

TABLE I-continued

Baseline and Change From Baseline in IOP (mm Hg) in Study of Example I

| | | | | | | | |
|---|---|---|---|---|---|---|---|
| Week 2 | 0 | Mean | −9.16 | −8.94 | −0.27 | −9.01 | −8.65 | −0.36 |
| | | SD | 3.280 | 3.162 | (−0.75, 0.21) | 3.245 | 3.327 | (−0.81, 0.09) |
| | 2 | Mean | −8.66 | −8.46 | −0.26 | −8.53 | −8.17 | −0.37 |
| | | SD | 3.593 | 3.188 | (−0.73, 0.20) | 3.688 | 3.368 | (−0.82, 0.07) |
| | 8 | Mean | −8.45 | −8.14 | −0.29 | −8.22 | −7.85 | −0.43 |
| | | SD | 3.377 | 3.062 | (−0.73, 0.16) | 3.507 | 3.290 | (−0.85, 0.00) |
| Week 6 | 0 | Mean | −8.93 | −9.03 | −0.01 | −8.89 | −8.79 | −0.12 |
| | | SD | 3.170 | 3.148 | (−0.47, 0.45) | 3.246 | 3.312 | (−0.57, 0.33) |
| | 2 | Mean | −8.71 | −8.60 | −0.38 | −8.69 | −8.22 | −0.54 |
| | | SD | 3.601 | 3.442 | (−0.84, 0.08) | 3.695 | 3.619 | (−0.98, −0.09) |
| | 8 | Mean | −7.99 | −8.05 | −0.09 | −7.94 | −7.80 | −0.23 |
| | | SD | 3.412 | 3.272 | (−0.54, 0.37) | 3.454 | 3.473 | (−0.67, 0.21) |
| Week 12 | 0 | Mean | −9.06 | −8.72 | −0.37 | −8.94 | −8.51 | −0.46 |
| | | SD | 3.216 | 3.088 | (−0.83, 0.10) | 3.290 | 3.253 | (−0.91, −0.01) |
| | 2 | Mean | −8.53 | −8.38 | −0.30 | −8.44 | −8.08 | −0.40 |
| | | SD | 3.520 | 3.297 | (−0.73, 0.14) | 3.646 | 3.504 | (−0.83, 0.03) |
| | 8 | Mean | −7.98 | −7.72 | −0.36 | −7.87 | −7.52 | −0.45 |
| | | SD | 3.435 | 3.172 | (−0.78, 0.07) | 3.496 | 3.362 | (−0.86, −0.03) |

| | | | Average Eye IOP[b] (ITT) | | |
|---|---|---|---|---|---|
| Visit | Hour | Statistic | GANFORT ® PF (N = 278) | GANFORT ® (N = 283) | Difference (95% CI)[e] |
| Baseline | 0 | Mean | 24.94 | 24.86 | 0.11 |
| | | SD | 2.116 | 2.131 | (−0.21, 0.43) |
| | 2 | Mean | 24.29 | 24.23 | 0.09 |
| | | SD | 2.515 | 2.426 | (−0.29, 0.46) |
| | 8 | Mean | 23.42 | 23.36 | 0.10 |
| | | SD | 2.904 | 2.703 | (−0.30, 0.51) |
| Week 2 | 0 | Mean | −8.72 | −8.37 | −0.40 |
| | | SD | 3.065 | 3.196 | (−0.88, 0.08) |
| | 2 | Mean | −8.24 | −8.00 | −0.33 |
| | | SD | 3.466 | 3.232 | (−0.82, 0.16) |
| | 8 | Mean | −7.94 | −7.53 | −0.49 |
| | | SD | 3.368 | 3.203 | (−0.97, −0.01) |
| Week 6 | 0 | Mean | −8.66 | −8.55 | −0.19 |
| | | SD | 3.052 | 3.153 | (−0.67, 0.29) |
| | 2 | Mean | −8.39 | −8.05 | −0.48 |
| | | SD | 3.467 | 3.424 | (−0.97, 0.02) |
| | 8 | Mean | −7.71 | −7.54 | −0.26 |
| | | SD | 3.324 | 3.340 | (−0.75, 0.22) |
| Week 12 | 0 | Mean | −8.65 | −8.30 | −0.45 |
| | | SD | 3.109 | 3.009 | (−0.92, 0.02) |
| | 2 | Mean | −8.11 | −7.86 | −0.38 |
| | | SD | 3.392 | 3.413 | (−0.87, 0.11) |
| | 8 | Mean | −7.57 | −7.27 | −0.43 |
| | | SD | 3.395 | 3.226 | (−0.92, 0.05) |

GANFORT ® PF = bimatoprost 0.3 mg/mL + timolol 5 mg/mL preservative-free;
IOP = intraocular pressure;
ITT = intent-to-treat;
PP = per protocol
In the ITT population, missing values were imputed using the last observation carried forward (LOCF) method.
[a]Worse eye refers to the eye with the worse baseline IOP, which was determined as the eye with the higher mean diurnal IOP at baseline. If both eyes had the same mean diurnal IOP at baseline, the right eye was designated as the worse eye.
[b]Average eye IOP refers to the average IOP of both eyes.
[c]Confidence intervals (CI) are based on the analysis of covariance (ANCOVA) model with treatment and investigator as main effects and baseline worse eye IOP as the covariate. Estimated difference (bimatoprost 0.3 mg/mL + timolol 5 mg/mL PF minus GANFORT ®) is based on the least-squares means from the ANCOVA model. If patients had baseline IOP value excluded due to protocol deviations then they were not included in the change from baseline analyses.
[d]CIs are based on the ANCOVA model with treatment and investigator as main effects and baseline worse eye IOP as the covariate. Estimated difference (bimatoprost 0.3 mg/mL + timolol 5 mg/mL PF minus GANFORT ®) is based on the least-squares means from the ANCOVA model.
[e]CIs are based on the analysis of variance (ANOVA) model with treatment and investigator as fixed effects. Estimated difference (bimatoprost 0.3 mg/mL + timolol 5 mg/mL PF minus GANFORT ®) is based on the least-squares means from the ANOVA model. Source: Clinical Study Report on file Other analysis of efficacy produced similar results. Hence Ganfort® PF, showed consistently numerically greater IOP reduction than Ganfort®.

Treatment in patients with glaucoma or OHT is aimed at lowering IOP in order to preserve visual function and hence quality of life. The impact of IOP reduction on disease progression have been well established (Kass et al, 2002; AGIS, 2000; Heijl et al, 2002), with data indicating that for each 1 mmHg of IOP reduction, the risk of progression is reduced by approximately 10% (Litchter, 2002; Leske et al, 2007). Preservative free formulations offer an alternative treatment for patients who are sensitive to preservatives or who have susceptibility to preservative-related ocular surface adverse events. However, with the known penetration enhancing effects of BAK, it is anticipated that a loss in efficacy will be seen, in which case the treating physician has to balance treatment tolerability for a particular patient versus the undesired loss of IOP lowering efficacy. The results of the above-described study, showing an increased TOP lowering effect of removal of BAK in the Ganfort® PF formulation is an unexpected finding that can benefit patients with glaucoma and OHT who often require efficacious, long term treatment.

BAK Effect

Given the known penetration enhancing effect of benzalkonium chloride (BAK), which is a preservative used in many marketed ophthalmic products, it was expected that Ganfort® Preservative Free (PF), which does not contain the 50 ppm BAK present in Ganfort®, would result in lower ocular bioavailability of both bimatoprost and timolol, and consequently be less effective in lowering TOP than Ganfort®. Therefore, data from the above described study contradicted conventional wisdom.

What is claimed is:

1. A preservative free composition for reducing intraocular pressure in a patient comprising: about 0.03% w/v bimatoprost, about 0.68% w/v timolol maleate, sodium phosphate dibasic heptahydrate, citric acid monohydrate, sodium chloride, and water, wherein the composition does not comprise a preservative; and,
    wherein the composition has a greater effect on reducing intraocular pressure than the same composition preserved with 50 ppm benzalkonium chloride.

2. The composition of claim 1, wherein the composition comprises 0.03% w/v bimatoprost, 0.68% w/v timolol maleate, 0.268% w/v sodium phosphate dibasic heptahydrate, 0.014% w/v citric acid monohydrate, 0.68% w/v sodium chloride, and water, the composition having a pH of about 7.3.

3. The composition of claim 1 or 2, where the patient has glaucoma or ocular hypertension.

4. The composition of claim 1 or 2, wherein the composition is applied once a day to at least one eye of the patient.

5. The composition of claim 1 or 2, wherein the composition is applied twice a day to at least one eye of the patient.

* * * * *